(12) United States Patent
Akerman et al.

(10) Patent No.: US 7,622,145 B2
(45) Date of Patent: Nov. 24, 2009

(54) METHOD OF COATING STENTS

(75) Inventors: Eugena A. Akerman, Bedminster, NJ (US); Dirk Cleeren, Merksem (BE); Gerard Llanos, Stewartsville, NJ (US); Cynthia A. Maryanoff, New Hope, PA (US); Georgios Papandreou, Kendall Park, NJ (US); William Rion, Ft. Lauderdale, FL (US); Karel Six, Hulste (BE); Thomas L. Todd, Parkland, FL (US)

(73) Assignee: Cordis Corporation, Miami Lakes, FL (US)

( * ) Notice: Subject to any disclaimer, the term of this patent is extended or adjusted under 35 U.S.C. 154(b) by 737 days.

(21) Appl. No.: 11/189,189

(22) Filed: Jul. 26, 2005

(65) Prior Publication Data

US 2006/0024426 A1 Feb. 2, 2006

Related U.S. Application Data

(60) Provisional application No. 60/591,472, filed on Jul. 27, 2004.

(51) Int. Cl.
*A61L 33/00* (2006.01)
(52) U.S. Cl. .............. 427/2.1; 427/2.24; 427/2.25; 427/2.28; 427/2.3; 427/231; 427/232; 427/233; 427/234; 427/335; 427/236; 427/238; 427/239; 427/294; 427/296; 427/377; 427/378; 427/398.4; 427/421; 427/424; 427/425; 623/1.16; 623/1.46; 623/1.34; 514/183; 522/153
(58) Field of Classification Search ............... 427/2.24, 427/255.6, 384, 2.3, 2.28; 522/153; 514/183; 623/1.16
See application file for complete search history.

(56) References Cited

U.S. PATENT DOCUMENTS

| 5,464,650 | A  | * | 11/1995 | Berg et al. | .............. 427/2.3 |
| 6,299,604 | B1 |   | 10/2001 | Ragheb et al. | |
| 6,586,048 | B2 | * | 7/2003  | Welch et al. | ............ 427/255.6 |
| 6,743,462 | B1 | * | 6/2004  | Pacetti | ................ 427/2.24 |
| 2002/0037944 | A1 | * | 3/2002 | Shen et al. | ............... 522/153 |
| 2002/0182392 | A1 |   | 12/2002 | Welch et al. | |
| 2003/0083646 | A1 |   | 5/2003  | Sirhan et al. | |
| 2003/0204245 | A1 | * | 10/2003 | Brightbill | ................ 623/1.16 |
| 2003/0207856 | A1 | * | 11/2003 | Tremble et al. | ............ 514/183 |
| 2004/0063805 | A1 |   | 4/2004  | Pacetti et al. | .............. 523/113 |

FOREIGN PATENT DOCUMENTS

WO     03/000308 A1    1/2003

(Continued)

OTHER PUBLICATIONS

Continuous PPV-containing films obtained from parylene develop yellow-green fluorescent colour on exposure to bromine vapour at elevateed temperature, Nov. 20, 1991, Derwent Information LTD.*

(Continued)

*Primary Examiner*—Michael Barr
*Assistant Examiner*—Andrew Bowman
(74) *Attorney, Agent, or Firm*—Carl J. Evens

(57) ABSTRACT

Processes for coating implantable medical devices that improve the stability of therapeutic agents contained within the coating.

18 Claims, 4 Drawing Sheets

Process Flow

FOREIGN PATENT DOCUMENTS

WO 03/079936 A1 10/2003

OTHER PUBLICATIONS

Anonymous, RD332081A, Dec. 1991, Derwent Information Ltd, abstract only.*
Anonymous, Continuos PPV-contg. films obtd. from parylene develop yellow-green fluorescent colour on exposure to bromine vapour at elevated temp., Dec. 10, 1991, Derwent Infformation LTD, (listed as RD332081A).*
Campbell et al., "Phenotypic Modulation fo Smooth Muscle Cells in Primary Culture", no. date provided, Vascular Smooth Muscle in Culture, vol. 1, pp. 39-52.*
Berk, B. C. et al., "Heparins and Glucocorticoids Inhibit Restenosis," J. Am. Coll. Cardiol., 1991, 17, 111B-117B.
Campbell, G. R., et al., "Smooth muscle phenotypic changes in arterial wall homeostasis: implications for the pathogenesis of atherosclerosis," Exp. Mol. Pathol., Apr. 1985, 42(2), 139-162.
Chang, M. W. et al., "Adenovirus-mediated Over-expression of the Cyclin/Cyclin-dependent," J. Clin. Invest., 1995, 96: 2260-2268.
Clowes, A. W. et al., "Kinetics of cellular proliferation after arterial injury. II. Inhibition of smooth muscle growth by heparin," Lab. Invest., 1985, 52(6), 611-616.
Clowes, A. W. et al., "Kinetics of cellular proliferation after arterial injury. IV. Heparin inhibits rat smooth muscle mitogenesis and migration," Circ. Res., 1986, 58(6), 839-845.
Clowes, A. W. et al., "Significance of quiescent smooth muscle migration in the injured rat carotid artery," Circ Res. 1985, 56(1), 139-145.
Clowes, A. W., "Suppression by heparin of smooth muscle cell proliferation in injured arteries," Nature, 1977, 265(5595), 625-626.
Colburn, M. D. et al., "Dose responsive suppression of myointimal hyperplasia by dexamethasone," J. Vasc. Surg., 1992, 15, 510-518.
Currier, J. W. et al., "Colchicine Inhibits Restenosis After Iliac Angioplasty in the Atherosclerotic Rabbit," Circ., 1989, 80(4), 11-66.
Edelman, E. R. et al., "Pathobiologic responses to stenting," Am J. Cardiol. 1998, 81(7A), 4E-6E.
Farb, A. et al., "Vascular smooth muscle cell cytotoxicity and sustained inhibition of neointimal formation by fibroblast growth factor 2-saporin fusion protein," Circ. Res., 1997, 80, 542-550.
Ferns, G. A. A. et al., "Inhibition of Neointimal Smooth Muscle Accumulation After Angioplasty by an Antibody to PDGF," Science, 1991, 253, 1129-1132.
Fischman, D. L. et al., "A Randomized Comparison of Coronary-Stent Placement and Balloon Angioplasty in the Treatment of Coronary Artery Disease," N. Eng. J. Med., Aug. 25, 1994, 331(8), 496-501.
Franklin, S. M. et al., "Pharmacologic prevention of restenosis after coronary angioplasty: review of the randomized clinical trails," Coron Artery Dis. Mar. 1993, 4(3), 232-242.
Fukuyama, J. et al., "Tranilast suppresses the vascular intimal hyperplasia after balloon injury in rabbits fed on a high-cholesterol diet," Eur. J. Pharmacol., 1996, 318, 327-332.
Guyton, J. R. et al., "Inhibition of rat arterial smooth muscle cell proliferation by heparin. In vivo studies with anticoagulant and nonanticoagulant heparin," Circ. Res., 1980, 46, 625-634.
Hansson, G. K. et al., "Interferon-γ Inhibits Arterial Stenosis After Injury," Circ., 1991, 84, 1266-1272.
Jonasson, J. et al., "Cyclosporin A inhibits smooth muscle proliferation in the vascular response to injury," Proc. Natl., Acad. Sci., 1988, 85, 2303-2306.
Lang, R. J. et al., "Effects of 2,3-butanedione monoxime on whole-cell Ca2+ channel currents in single cells of the guinea-pig taenia caeci," J Physiol. Feb. 1991, 433, 1-24.
Lang, R. J. et al., "Effects of okadaic acid and ATP gamma S on cell length and Ca(2+)-channel currents recorded in single smooth muscle cells of the guinea-pig taenia caeci.,", Br. J. Pharmacol., Oct. 1991, 104(2), 331-336.
Liu, M. W. et al., "Trapidil in Preventing Restenosis After Balloon Angioplasty in the Atherosclerotic Rabbit," Circ., 1990, 81, 1089-1093.
Lundergan, C. F. et al., "Terbinafine inhibits the mitogenic response to platelet-derived growth factor in vitro and neointimal proliferation in vivo," Am. J. Cardiol., 1991, 17(Suppl. B), 132B-136B.

Majesky, M. W. et al., "Heparin regulates smooth muscle S phase entry in the injured rat carotid artery," Circ. Res., 1987, 61, 296-300.
Mak, K-H. et al., "Clinical trials to prevent restenosis after percutaneous coronary revascularization," Ann N Y Acad Sci., Apr. 15, 1997, 255-84; discussion 284-8. Review.
Marx, S. O. et al., "Rapamycin-FKBP Inhibits Cell Cycle Regulators of Proliferation in Vascular Smooth Muscle Cells," Circ. Res., 1995, 76, 412-417.
Nemecek, G. M. et al., "Terbinafine Inhibits the Mitogenic Response to Platelet-Derived Growth Factor in Vitro and Neoinimal Proliferation in Vivo," J. Pharmacol. Exp. Thera., 1989, 248, 1167-1174.
Okada, T. et al., "Localized Release of Perivascular Heparin Inhibits Intimal Proliferation after Endothelial Injury without Systemic Anticoagulation," Neurosurgery, 1989, 25, 92-98.
Popma, J. J. et al , "Atherectomy of right coronary ostial stenoses: initial and long-term results, technical features and histologic findings," Am J Cardiol., Feb. 15, 1991; 67(5), 431-3.
Popma, J. J. et al., "Adjuncts to thrombolysis for myocardial reperfusion," Ann Intern Med., Jul. 1, 1991, 115(1), 34-44.
Popma, J. J. et al., "Clinical trials of restenosis after coronary angioplasty," Circulation, Sep. 1991, 84(3), 1426-1436.
Popma, J. J. et al., "Clinical, angiographic and procedural correlates of quantitative coronary dimensions after directional coronary atherectomy," J Am Coll Cardiol., Nov. 1, 1991, 18(5), 1183-1189.
Powell, J. S. et al., "Inhibitors of Angiotensin-Converting Enzyme Prevent Myointimal Proliferation After Vascular Injury," Science, 1989, 245, 186-188.
Serruys, P. W. et al., "A comparison of balloon-expandable-stent implantation with balloon angioplasty in patients with coronary artery disease," N Engl J Med, Aug. 25, 1994; 331(8), 489-495.
Serruys, P. W. et al., "Evaluation of ketanserin in the prevention of restenosis after percutaneous transluminal coronary angioplasty. A multicenter randomized double-blind placebo-controlled trial," Circulation. Oct. 1993; 88(4 Pt 1), 1588-1601.
Serruys, P. W. et al., "Heparin-coated Palmaz-Schatz stents in human coronary arteries. Early outcome of the Benestent-II Pilot Study," Circulation, Feb. 1, 1996; 93(3), 412-422.
Serruys, P. W. et al., "Restenosis revisited: insights provided by Quantitative coronary angiography," Am Heart J, Nov. 1993; 126(5), 1243-1267.
Serruys, P. W. et al., "The bailout stent. Is a friend in need always a friend indeed?" Circulation, Nov. 1993; 88(5 Pt 1), 2455-2457.
Surruys, P. W. et al., "Randomized Trials of Coronary Stenting," *Journal of Interventional Cardiology*, 1994, 7(4), 331.
Simons, M. et al., "Antisense c-*myb* oligonucleotides inhibit intimal arterial smooth muscle cell accumulation in vivo," Nature, 1992, 359, 67-70.
Snow, A. D. et al., "Heparin modulates the composition of the extracellular matrix domain surrounding arterial smooth muscle cells," Am. J. Pathol., 1990, 137, 313-330.
Sollot, S. J. et al., "Taxol Inhibits Neointimal Smooth Muscle Cell Accumulation after Angioplasty in the Rat," J. Clin. Invest., 1995, 95, 1869-1876.
Tanaka, H. et al., "Sustained activation of vascular cells and leukocytes in the rabbit aorta after balloon injury," Circulation, Oct. 1993; 88(4 Pt 1), 1788-1803.
Tardif, et al., "Probucol and multivitamins in the prevention of restenosis after coronary angioplasty. Multivitamins and Probucol Study Group," N Engl J Med. Aug 7, 1997; 337(6), 365-372.
Teirstein, P. S. et al., "Catheter-based radiotherapy to inhibit restenosis after coronary stenting," N. Engl J Med., Jun. 12, 1997; 336(24), 1697-1703.
Weinberger, J. et al., "Intracoronary irradiation: dose response for the prevention of restenosis in swine," Int. J. Rad. Onc. Biol. Phys., 1996, 36, 767-775.
Yokoi, H. et al., "Effectiveness of an antioxidant in preventing restenosis after percutaneous transluminal coronary angioplasty: the Probucol Angioplasty Restenosis Trial," J Am Coll Cardiol., Oct. 1997; 30(4), 855-862.
European Search Report EP 05 25 4517 dated Nov. 30, 2005.
International Search Report PCT/US2005/026450 dated May 31, 2006.

* cited by examiner

METHOD OF COATING STENTS

CROSS REFERENCE TO RELATED APPLICATIONS

This application claims the benefit of prior U.S. Provisional Patent Application Ser. No. 60/591,472 filed Jul. 27, 2004.

BACKGROUND OF THE INVENTION

1. Field of the Invention

The present invention relates to methods for coating stents, and more particularly to methods for coating stents with therapeutic agents.

2. Discussion of the Related Art

Many individuals suffer from circulatory disease caused by a progressive blockage of the blood vessels that profuse the heart and other major organs. More severe blockage of blood vessels in such individuals often leads to hypertension, ischemic injury, stroke, or myocardial infarction. Atherosclerotic lesions, which limit or obstruct coronary blood flow, are the major cause of ischemic heart disease. Percutaneous transluminal coronary angioplasty is a medical procedure whose purpose is to increase blood flow through an artery. Percutaneous transluminal coronary angioplasty is the predominant treatment for coronary vessel stenosis. The increasing use of this procedure is attributable to its relatively high success rate and its minimal invasiveness compared with coronary bypass surgery. A limitation associated with percutaneous transluminal coronary angioplasty is the abrupt closure of the vessel, which may occur immediately after the procedure and restenosis, which occurs gradually following the procedure. Additionally, restenosis is a chronic problem in patients who have undergone saphenous vein bypass grafting. The mechanism of acute occlusion appears to involve several factors and may result from vascular recoil with resultant closure of the artery and/or deposition of blood platelets and fibrin along the damaged length of the newly opened blood vessel.

Restenosis after percutaneous transluminal coronary angioplasty is a more gradual process initiated by vascular injury. Multiple processes, including thrombosis, inflammation, growth factor and cytokine release, cell proliferation, cell migration and extracellular matrix synthesis each contribute to the restenotic process.

While the exact mechanism of restenosis is not completely understood, the general aspects of the restenosis process have been identified. In the normal arterial wall, smooth muscle cells proliferate at a low rate, approximately less than 0.1 percent per day. Smooth muscle cells in the vessel walls exist in a contractile phenotype characterized by eighty to ninety percent of the cell cytoplasmic volume occupied with the contractile apparatus. Endoplasmic reticulum, Golgi, and free ribosomes are few and are located in the perinuclear region. An extracellular matrix surrounds the smooth muscle cells and is rich in heparin-like glycosylaminoglycans, which are believed to be responsible for maintaining smooth muscle cells in the contractile phenotypic state (Campbell and Campbell, 1985).

Upon pressure expansion of an intracoronary balloon catheter during angioplasty, smooth muscle cells within the vessel wall become injured, initiating a thrombotic and inflammatory response. Cell derived growth factors such as platelet derived growth factors, basic fibroblast growth factors, epidermal growth factors, thrombin, etc., released from platelets, invading macrophages and/or leukocytes, or directly from the smooth muscle cells provoke a proliferative and migratory response in medial smooth muscle cells. These cells undergo a change from the contractile phenotype to a synthetic phenotype characterized by only a few contractile filament bundles, extensive rough endoplasmic reticulum, Golgi and free ribosomes. Proliferation/migration usually begins within one to two days' post-injury and peaks several days thereafter (Campbell and Campbell, 1987; Clowes and Schwartz, 1985).

Daughter cells migrate to the intimal layer of arterial smooth muscle and continue to proliferate and secrete significant amounts of extracellular matrix proteins. Proliferation, migration and extracellular matrix synthesis continue until the damaged endothelial layer is repaired at which time proliferation slows within the intima, usually within seven to fourteen days post-injury. The newly formed tissue is called neointima. The further vascular narrowing that occurs over the next three to six months is due primarily to negative or constrictive remodeling.

Simultaneous with local proliferation and migration, inflammatory cells adhere to the site of vascular injury. Within three to seven days post-injury, inflammatory cells have migrated to the deeper layers of the vessel wall. In animal models employing either balloon injury or stent implantation, inflammatory cells may persist at the site of vascular injury for at least thirty days (Tanaka et al., 1993; Edelman et al., 1998). Inflammatory cells therefore are present and may contribute to both the acute and chronic phases of restenosis.

Numerous agents have been examined for presumed antiproliferative actions in restenosis and have shown some activity in experimental animal models. Some of the agents which have been shown to successfully reduce the extent of intimal hyperplasia in animal models include: heparin and heparin fragments (Clowes, A. W. and Karnovsky M., Nature 265: 25-26, 1977; Guyton, J. R. et al., Circ. Res., 46: 625-634, 1980; Clowes, A. W. and Clowes, M. M., Lab. Invest. 52: 611-616, 1985; Clowes, A. W. and Clowes, M. M., Circ. Res. 58: 839-845, 1986; Majesky et al., Circ. Res. 61: 296-300, 1987; Snow et al., Am. J. Pathol. 137: 313-330, 1990; Okada, T. et al., Neurosurgery 25: 92-98, 1989), colchicine (Currier, J. W. et al., Circ. 80: 11-66, 1989), taxol (Sollot, S. J. et al., J. Clin. Invest. 95: 1869-1876, 1995), angiotensin converting enzyme (ACE) inhibitors (Powell, J. S. et al., Science, 245: 186-188, 1989), angiopeptin (Lundergan, C. F. et al. Am. J. Cardiol. 17(Suppl. B):132B-136B, 1991), cyclosporin A (Jonasson, L. et al., Proc. Natl., Acad. Sci., 85: 2303, 1988), goat-anti-rabbit PDGF antibody (Ferns, G. A. A., et al., Science 253: 1129-1132, 1991), terbinafine (Nemecek, G. M. et al., J. Pharmacol. Exp. Thera. 248: 1167-1174, 1989), trapidil (Liu, M. W. et al., Circ. 81: 1089-1093, 1990), tranilast (Fukuyama, J. et al., Eur. J. Pharmacol. 318: 327-332, 1996), interferon-gamma (Hansson, G. K. and Holm, J., Circ. 84: 1266-1272, 1991), rapamycin (Marx, S. O. et al., Circ. Res. 76: 412-417, 1995), steroids (Colburn, M. D. et al., J. Vasc. Surg. 15: 510-518, 1992), see also Berk, B. C. et al., J. Am. Coll. Cardiol. 17: 111B-117B, 1991), ionizing radiation (Weinberger, J. et al., Int. J. Rad. One. Biol. Phys. 36: 767-775, 1996), fusion toxins (Farb, A. et al., Circ. Res. 80: 542-550, 1997) antisense oligonucleotides (Simons, M. et al., Nature 359: 67-70, 1992) and gene vectors (Chang, M. W. et al., J. Clin. Invest. 96: 2260-2268, 1995). Anti-proliferative action on smooth muscle cells in vitro has been demonstrated for many of these agents, including heparin and heparin conjugates, taxol, tranilast, colchicine, ACE inhibitors, fusion toxins, antisense oligonucleotides, rapamycin and ionizing radiation. Thus, agents with diverse mechanisms of smooth muscle cell inhibition may have therapeutic utility in reducing intimal hyperplasia.

However, in contrast to animal models, attempts in human angioplasty patients to prevent restenosis by systemic pharmacologic means have thus far been unsuccessful. Neither aspirin-dipyridamole, ticlopidine, anti-coagulant therapy (acute heparin, chronic warfarin, hirudin or hirulog), thromboxane receptor antagonism nor steroids have been effective in preventing restenosis, although platelet inhibitors have been effective in preventing acute reocclusion after angioplasty (Mak and Topol, 1997; Lang et al., 1991; Popma et al., 1991). The platelet GP $II_b/III_a$ receptor, antagonist, Reopro® is still under study, but Reopro® has not shown definitive results for the reduction in restenosis following angioplasty and stenting. Other agents, which have also been unsuccessful in the prevention of restenosis, include the calcium channel antagonists, prostacyclin mimetics, angiotensin converting enzyme inhibitors, serotonin receptor antagonists, and anti-proliferative agents. These agents must be given systemically, however, and attainment of a therapeutically effective dose may not be possible, and anti-proliferative (or anti-restenosis) concentrations may exceed the known toxic concentrations of these agents so that levels sufficient to produce smooth muscle inhibition may not be reached (Mak and Topol, 1997; Lang et al., 1991; Popma et al., 1991).

Additional clinical trials in which the effectiveness for preventing restenosis utilizing dietary fish oil supplements or cholesterol lowering agents have been examined showing either conflicting or negative results so that no pharmacological agents are as yet clinically available to prevent post-angioplasty restenosis (Mak and Topol, 1997; Franklin and Faxon, 1993: Serruys, P. W. et al., 1993). Recent observations suggest that the antilipid/antioxident agent, probucol, may be useful in preventing restenosis but this work requires confirmation (Tardif et al., 1997; Yokoi, et al., 1997). Probucol is presently not approved for use in the United States and a thirty-day pretreatment period would preclude its use in emergency angioplasty. Additionally, the application of ionizing radiation has shown significant promise in reducing or preventing restenosis after angioplasty in patients with stents (Teirstein et al., 1997). Currently, however, the most effective treatments for restenosis are repeat angioplasty, atherectomy or coronary artery bypass grafting, because no therapeutic agents currently have Food and Drug Administration approval for use for the prevention of post-angioplasty restenosis.

Unlike systemic pharmacologic therapy, stents have proven useful in significantly reducing restenosis. Typically, stents are balloon-expandable slotted metal tubes (usually, but not limited to, stainless steel), which, when expanded within the lumen of an angioplastied coronary artery, provide structural support through rigid scaffolding to the arterial wall. This support is helpful in maintaining vessel lumen patency. In two randomized clinical trials, stents increased angiographic success after percutaneous transluminal coronary angioplasty, by increasing minimal lumen diameter and reducing, but not eliminating, the incidence of restenosis at six months (Serruys et al., 1994; Fischman et al., 1994).

Additionally, the heparin coating of stents appears to have the added benefit of producing a reduction in sub-acute thrombosis after stent implantation (Serruys et al., 1996). Thus, sustained mechanical expansion of a stenosed coronary artery with a stent has been shown to provide some measure of restenosis prevention, and the coating of stents with heparin has demonstrated both the feasibility and the clinical usefulness of delivering drugs locally, at the site of injured tissue.

As stated above, the use of heparin coated stents demonstrates the feasibility and clinical usefulness of local drug delivery; however, the manner in which the particular drug or drug combination is affixed to the local delivery device will play a role in the efficacy of this type of treatment. For example, the processes and materials utilized to affix the drug/drug combinations to the local delivery device should not interfere with the operations of the drug/drug combinations. In addition, the processes and materials utilized should be biocompatible and maintain the drug/drug combinations on the local device through delivery and over a given period of time. For example, removal of the drug/drug combination during delivery of the local delivery device may potentially cause failure of the device.

Accordingly, there exists a need for drug/drug combinations and associated local delivery devices for the prevention and treatment of vascular injury causing intimal thickening which is either biologically induced, for example, atherosclerosis, or mechanically induced, for example, through percutaneous transluminal coronary angioplasty. In addition, there exists a need for maintaining the drug/drug combinations on the local delivery device through delivery and positioning as well as for ensuring that the drug/drug combination is released in therapeutic dosages over a given period of time.

A variety of stent coatings and compositions have been proposed for the prevention and treatment of injury causing intimal thickening. The coatings may be capable themselves of reducing the stimulus the stent provides to the injured lumen wall, thus reducing the tendency towards thrombosis or restenosis. Alternately, the coating may deliver a pharmaceutical/therapeutic agent or drug to the lumen that reduces smooth muscle tissue proliferation or restenosis. The mechanism for delivery of the agent is diffusion of the agent through either a bulk polymer or through pores that are created in the polymer structure, or by erosion of a biodegradable coating.

Both bioabsorbable and biostable compositions have been reported as coatings for stents. They generally have been polymeric coatings that either encapsulate a pharmaceutical/therapeutic agent or drug, e.g. rapamycin, taxol etc., or bind such an agent to the surface, e.g. heparin-coated stents. These coatings are applied to the stent in a number of ways, including, though not limited to, dip, spray, or spin coating processes.

While the selection of an appropriate therapeutic agent and an appropriate coating in which to incorporate the therapeutic agent is important, maintaining the stability of the agent is also important. Accordingly, there exists a need for developing a process for coating the implantable medical device that incorporates steps to stabilize the therapeutic agent.

SUMMARY OF THE INVENTION

The process of the present invention provides a means for overcoming the difficulties associated with the coating of implantable medical devices with therapeutic agents.

In accordance with one aspect, the present invention is directed to a process for coating implantable medical devices. The method comprises applying a primer coating on the implantable medical devices, including the application of a parylene layer and annealing the parylene layer to reduce autoxidation initiators, preparing a basecoat solution comprising polymers and a therapeutic agent and applying the basecoat solution to the implantable medical devices coated with parylene, the basecoat solution being prepared with and applied utilizing a process to reduce the presence and exposure of the basecoat solution to oxygen, preparing a topcoat solution comprising at least one polymer and applying the topcoat solution to the implantable medical devices coated with the basecoat solution, the topcoat solution being prepared with and applied utilizing a process to reduce the presence and exposure of the topcoat solution to oxygen, applying a solvent that has the potential to redissolve all coating components, creating a coating morphology to protect the therapeutic agent from autoxidation, and finally processing the implantable medical devices, including inspecting, packaging and sterilizing the coated medical devices, the final processing including protecting the therapeutic agent from autoxidation, reducing the presence of and exposure of all materials to free radicals and reducing the presence of and exposure of all materials to oxygen.

The process of the present invention incorporates a number of steps to increase the stability of the therapeutic agent, including protecting the therapeutic agent from autoxidation by increasing the glass transition temperature of the agent, reducing the presence of and/or exposure of various materials utilized to free radicals and autoxidation initiators and reducing the presence of and/or exposure of the various materials to oxygen.

BRIEF DESCRIPTION OF THE DRAWINGS

The foregoing and other features and advantages of the invention will be apparent from the following, more particular description of preferred embodiments of the invention, as illustrated in the accompanying drawings.

DETAILED DESCRIPTION OF THE PREFERRED EMBODIMENTS

Figure 1:
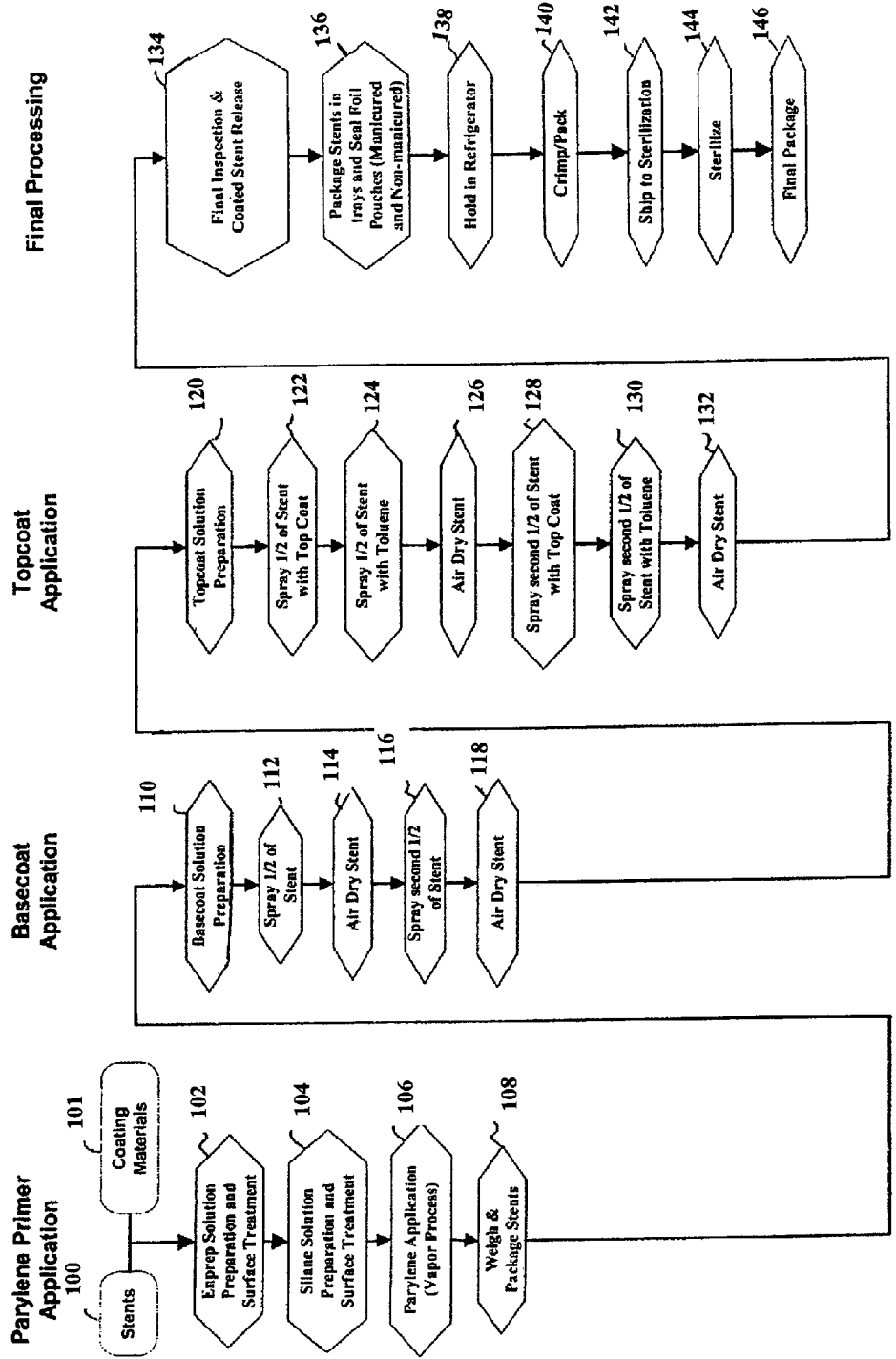
FIG. 1 is a flow chart of a first exemplary embodiment of a process for coating stents in accordance with the present invention.

The present invention is directed to a process for coating stents or other implantable medical devices with one or more therapeutic agents, such as a rapamycin. One exemplary process is set forth in the flow chart of FIG. 1. The first part of the process comprises the primer application. In the exemplary embodiment, the first step in the process is the provision of stents, step 100. and coating materials, step 101, and then surface preparation and treatment thereof, step 102. Step 102 involves utilizing a cleaning solution to remove endotoxins from the stents to be coated. The cleaning solution may comprise any number of cleaning solutions, for example, a high pH solution such as a potassium hydroxide solution containing silicates. The next step is also a surface preparation and treatment step, step 104. In step 104 a silane solution, such as an unsaturated organosilane solution, for example, is utilized to prepare the surfaces of the stents for the deposition of a primer layer. The next step is the application of the primer itself, step 106. In this exemplary embodiment, parylene is applied to the stents utilizing a vapor deposition process. Once the parylene is applied, the stents are packaged and weighed, step 108. Once the stents are weighed, they are placed in containers or vials. The vials may be formed from any number of suitable materials. In the exemplary embodiment, the vials are formed from polypropylene.

The second part of the process comprises the basecoat application. The first step in the second part of the process is the preparation of the basecoat, step 110. The basecoat may comprise any suitable biocompatible polymers and therapeutic agents. The therapeutic agents and polymers should preferably be compatible. In the exemplary embodiment, the basecoat solution comprises any of polyethylene co-vinylacetate, polybutylmethacrylate and a rapamycin, such as sirolimus. The solution is prepared in a standard reactor. The solution is decanted into smaller containers for the next step. The next step is the coating of the stents, step 112. In this step, the stents are coated with the basecoat solution. The stents may be coated in any suitable manner. In the exemplary embodiment, the stents are coated utilizing a spray coating technique. Nitrogen is utilized as the carrier gas for the basecoat solution. In step 112, one half of the stent is coated and then air dried in step 114. The half coated stents are dried at a relative humidity of about thirty to about fifty-five percent for a minimum of thirty minutes. The air temperature is held at about room temperature. The air in the drying chamber is continuously recirculated. Upon completion of the drying step 114, the second half of the stent is coated, step 116 and then dried again in step 118. Steps 116 and 118 are identical to steps 112 and 114. Of course, the artisan will appreciate that the basecoat could instead be applied to the stent at once.

The third part of the process comprises the topcoat application. The first step in the third part of the process is the preparation of the topcoat solution, step 120. The preparation of the topcoat comprises preparing a solution of polybutylmethacrylate. Once the solution is prepared and decanted into a spraying container, one-half of the stent is coated, step 122. The next step of the process is another coating step, step 124. In this coating step, the half of the stents that have been topcoated are sprayed with toluene. Toluene has the potential to partially redissolve all coating components and will alter the surface finish and the dissolution properties of the therapeutic agent. Of course, the artisan will readily appreciate that solvents other than toluene may also be used to achieve the same or similar effects. The spraying of a solvent such as toluene has a polishing effect on the topcoat and also facilitates elution control of the therapeutic agent from the polymeric coating. Once step 124 is complete, the stents are air dried, step 126, under the same conditions as in steps 114 and 118. Steps 128, 130 and 132 are the same as steps 122, 124 and 126 but for the second half of the stents. Of course, the artisan will appreciate that the topcoat could instead be applied to the stent at once.

The fourth and final part of the exemplary process comprises the final processing. The first step in the fourth part of the process is final inspection and coated stent release, step 134, wherein each of the stents is inspected for defects. Various inspection techniques such as microscopy may be utilized to determine if the stents meet various rigorous standards. The next step in the process is packaging, step 136. The stents are put into trays and sealed in pouches. In this exemplary embodiment, the trays are PETG trays. Once the stents are packaged, they are refrigerated, step 138. The stents are maintained at a temperature from about five degrees centigrade to about eight degrees centigrade. Wider ranges may be utilized. The next step in the process is the crimping and packaging of each of the stents, step 140. In this step, the stents are positioned on the delivery device and crimped to the desired size. Once positioned on the delivery devices, the whole system is packaged and shipped to a location for sterilization, steps 142 and 144. The systems are sterilized utilizing ethylene oxide, but other suitable sterilization processes may be utilized. The final step of the process is final packaging, step 146.

Figure 2:
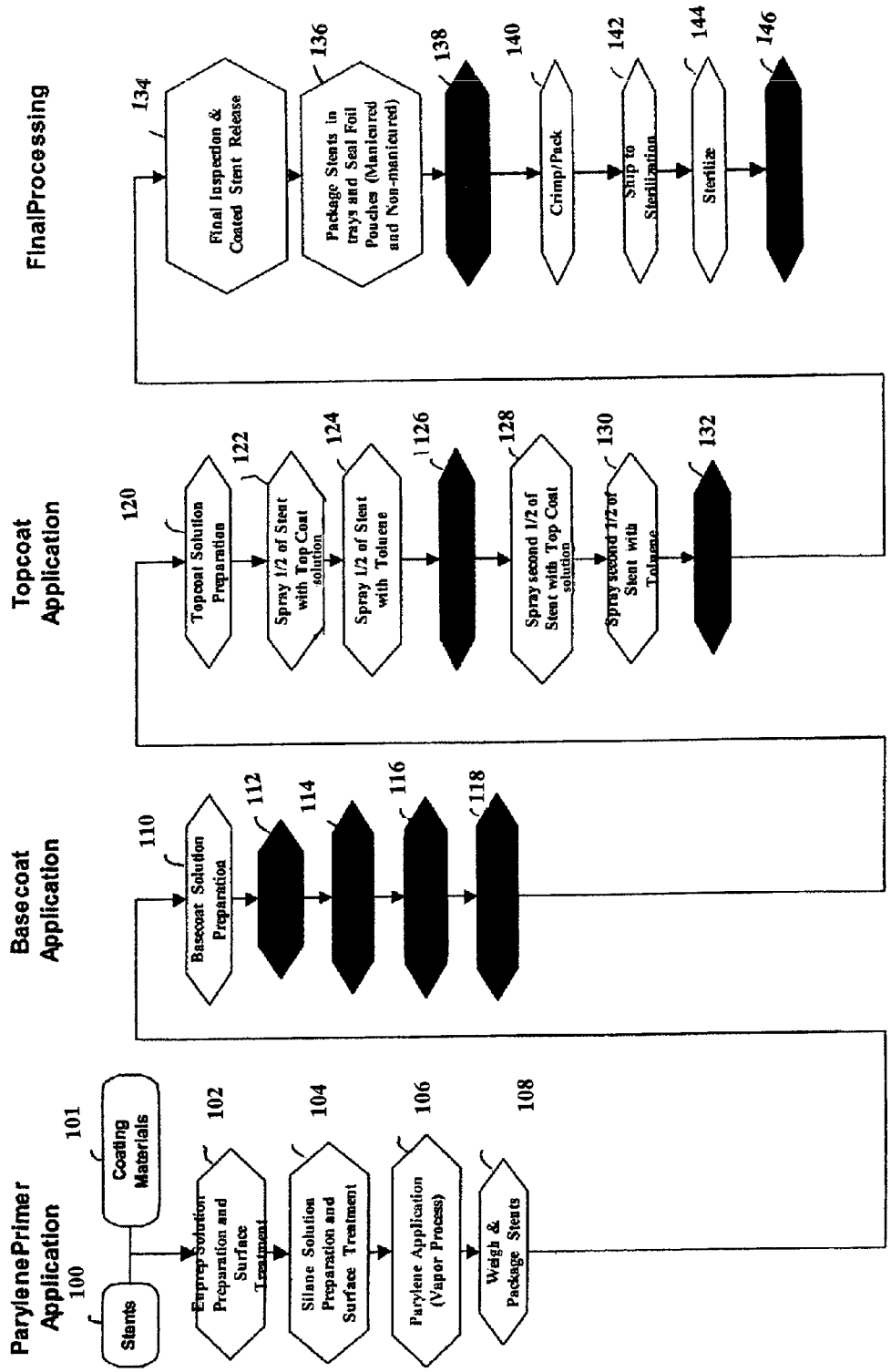
FIG. 2 is a flow chart of a second exemplary embodiment of a process for coating stents in accordance with the present invention.

A number of process modifications may be utilized to address autoxidation. Autoxidation occurs when there is a fuel, in this case the therapeutic agent, an ignition of the fuel, in this case radicals, and finally oxygen or oxygen containing compounds. The first process modification includes protecting the active pharmaceutic ingredient or therapeutic agent, for example sirolimus, from autoxidation. When an organic molecule is in the amorphous solid state, one way in which to reduce its reactivity is to raise its glass transition temperature, Tg. A higher glass transition temperature leads to a more stable therapeutic agent at room temperature. Amorphous substances may act like sponges and pick up other compounds such as solvents. Sirolimus is an amorphous therapeutic agent. Accordingly, in order to make an amorphous therapeutic agent more stable, one has to raise its glass transition temperature and since solvents lower the glass transition temperature, the minimization of exposure to residual solvents is required. Ways in which to reduce or minimize exposure to residual solvents include keeping extraneous solvents away from the coating, for example, cleaning agents and solvent bottles, and storing stents in an environment that is substantially solvent free, for example, away from freshly coated stents and/or from solutions. In addition, a higher glass transition temperature may be achieved by increasing the removal of residual solvents post coating. This may be accomplished by allowing more time for residual solvent removal post coating, by applying vacuum conditions and heat to enhance residual solvent removal and by allowing short-term moisture exchange (presence of humidity) to enhance residual solvent removal. The long-term exposure to high humidity is preferably controlled because humidity may act as a plasticizer and/or cause hydrolysis reactions. Vacuum packaging and packaging under inert gas of the finished goods addresses this concern. The spraying conditions may be modified to control or affect the coating morphology, for example, low humidity and spray head distance. The steps of the process that may be modified to accomplish these improvements include steps 112, 114, 116, 118, 126, 132, 138 and 146 as illustrated in FIG. 2.

Figure 3:
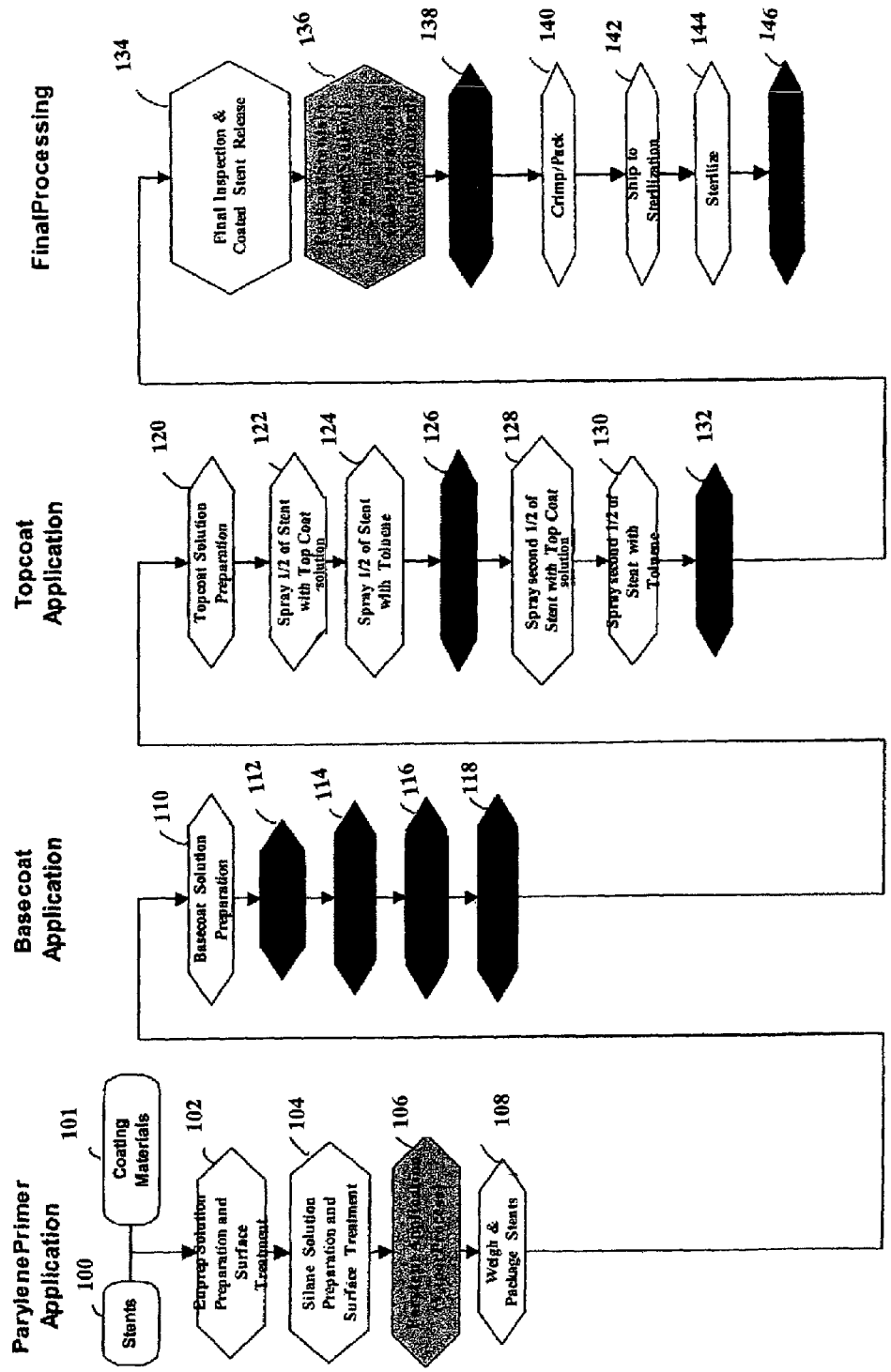
FIG. 3 is a flow chart of a third exemplary embodiment of a process for coating stents in accordance with the present invention.

Another process modification comprises reducing the presence of and/or exposure to free radicals and, autoxidation initiators. This may be accomplished by utilizing materials that will contact the coating with minimal exposure to free radicals, for example, polypropylene vials may be utilized rather than PETG trays, and utilizing tools to assist in the crimping and packaging stage that are fabricated from inert materials. This may also be accomplished by parylene annealing to reduce parylene radicals. The steps of the process that may be modified to accomplish these improvements include steps 106 and 136 as illustrated in FIG. 3.

Figure 4:
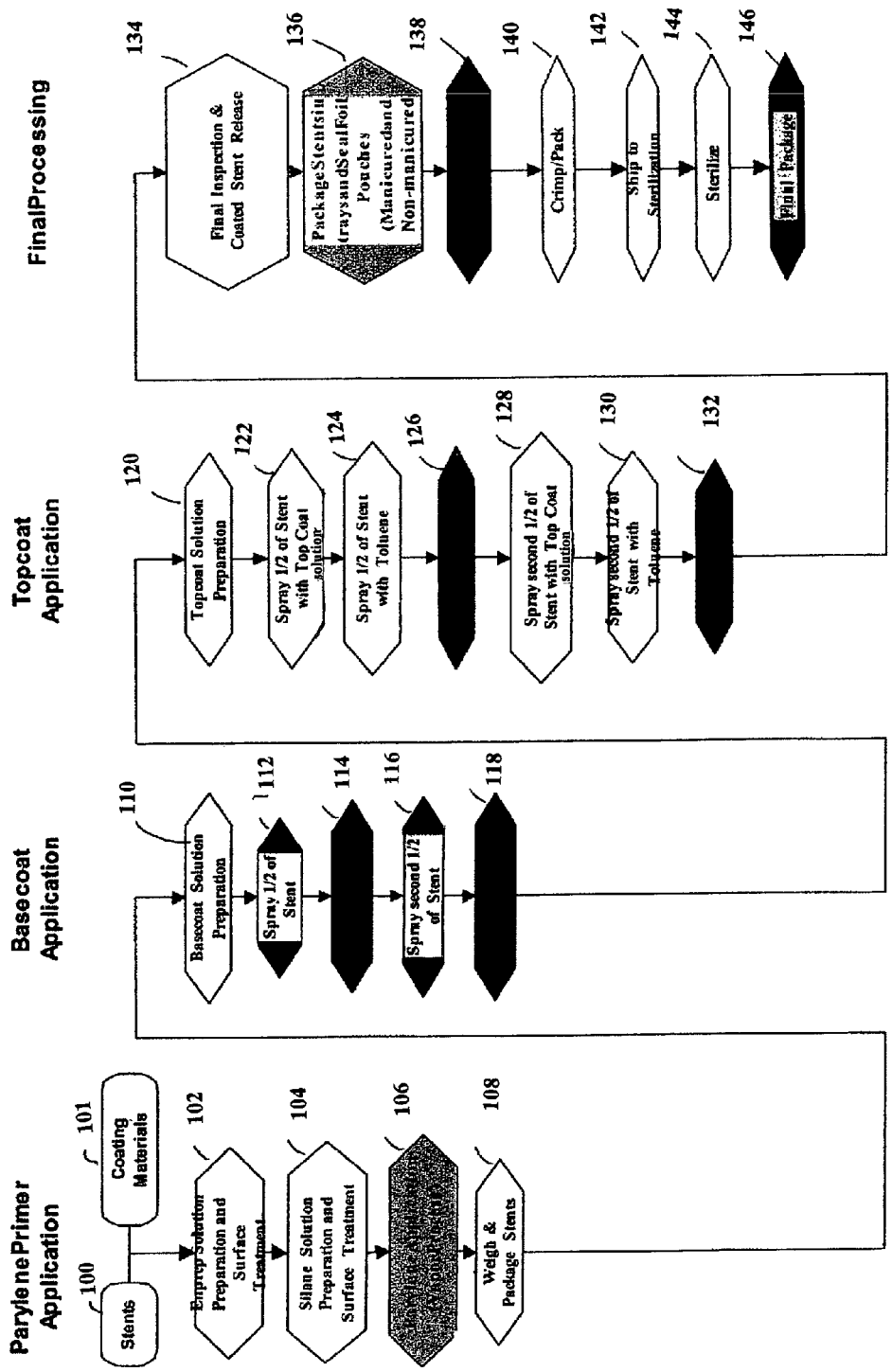
FIG. 4 is a flow chart of a fourth exemplary embodiment of a process for coating stents in accordance with the present invention.

Yet another process modification comprises reducing the presence of and/or exposure to oxygen. This may be accomplished by having improved controls of raw materials, improved coating solution mixing and handling, and improved coatings. Improved control of raw materials includes solvents such as THF with low hydroperoxides. Improved coating solution mixing and handling includes inert gas blanketing to reduce dissolved oxygen and the minimization of all decanting steps. Improved coating includes spraying in a nitrogen rich environment, vacuum oven, purging with inert gas after annealing and vacuum packaging, and/or packaging under inert gas of works in progress and finished goods. The steps of the process that may be modified to accomplish these improvements include steps 101, 110, 112, 116, 120, 136 and 146 as illustrated in FIG. 4.

It is important to note that although stents are discussed in detail herein, the local delivery of drug/drug combinations may be utilized to treat a wide variety of conditions utilizing any number of medical devices, or to enhance the function and/or life of the device. For example, intraocular lenses, placed to restore vision after cataract surgery is often compromised by the formation of a secondary cataract. The latter is often a result of cellular overgrowth on the lens surface and can be potentially minimized by combining a drug or drugs with the device. Other medical devices which often fail due to tissue in-growth or accumulation of proteinaceous material in, on and around the device, such as shunts for hydrocephalus, dialysis grafts, colostomy bag attachment devices, ear drainage tubes, leads for pace makers and implantable defibrillators can also benefit from the device-drug combination approach. Devices which serve to improve the structure and function of tissue or organ may also show benefits when combined with the appropriate agent or agents. For example, improved osteointegration of orthopedic devices to enhance stabilization of the implanted device could potentially be achieved by combining it with agents such as bone-morphogenic protein. Similarly other surgical devices, sutures, staples, anastomosis devices, vertebral disks, bone pins, suture anchors, hemostatic barriers, clamps, screws, plates, clips, vascular implants, tissue adhesives and sealants, tissue scaffolds, various types of dressings, bone substitutes, intraluminal devices, and vascular supports could also provide enhanced patient benefit using this drug-device combination approach. Essentially, any type of medical device may be coated in some fashion with a drug or drug combination which enhances treatment over use of the singular use of the device or pharmaceutical agent.

In addition to various medical devices, the coatings on these devices may be used to deliver therapeutic and pharmaceutic agents including: antiproliferative/antimitotic agents including natural products such as vinca alkaloids (i.e. vinblastine, vincristine, and vinorelbine), paclitaxel, epidipodophyllotoxins (i.e. etoposide, teniposide), antibiotics (dactinomycin (actinomycin D) daunorubicin, doxorubicin and idarubicin), anthracyclines, mitoxantrone, bleomycins, plicamycin (mithramycin) and mitomycin, enzymes (L-asparaginase which systemically metabolizes L-asparagine and deprives cells which do not have the capacity to synthesize their own asparagine); antiplatelet agents such as G(GP) $II_b$/$III_a$ inhibitors and vitronectin receptor antagonists; antiproliferative/antimitotic alkylating agents such as nitrogen mustards (mechlorethamine, cyclophosphamide and analogs, melphalan, chlorambucil), ethylenimines and methylmelamines (hexamethylmelamine and thiotepa), alkyl sulfonates-busulfan, nitrosoureas (carmustine (BCNU) and analogs, streptozocin), triazenes-dacarbazinine (DTIC); antiproliferative/antimitotic antimetabolites such as folic acid analogs (methotrexate), pyrimidine analogs (fluorouracil, floxuridine, and cytarabine), purine analogs and related inhibitors (mercaptopurine, thioguanine, pentostatin and 2-chlorodeoxyadenosine {cladribine}); platinum coordination complexes (cisplatin, carboplatin), procarbazine, hydroxyurea, mitotane, aminoglutethimide; hormones (i.e. estrogen); anticoagulants (heparin, synthetic heparin salts and other inhibitors of thrombin); fibrinolytic agents (such as tissue plasminogen activator, streptokinase and urokinase), aspirin, dipyridamole, ticlopidine, clopidogrel, abciximab; antimigratory; antisecretory (breveldin); anti-inflammatory: such as adrenocortical steroids (cortisol, cortisone, fludrocortisone, prednisone, prednisolone, 6α-methylprednisolone, triamcinolone, betamethasone, and dexamethasone), nonsteroidal agents (salicylic acid derivatives i.e. aspirin; para-aminophenol derivatives i.e. acetominophen; indole and indene acetic acids (indomethacin, sulindac, and etodalac), heteroaryl acetic acids (tolmetin, diclofenac, and ketorolac), arylpropionic acids (ibuprofen and derivatives), anthranilic acids (mefenamic acid, and meclofenamic acid), enolic acids (piroxicam, tenoxicam, phenylbutazone, and oxyphenthatrazone), nabumetone, gold compounds (auranofin, aurothioglucose, gold sodium thiomalate); immunosuppressives: (cyclosporine, tacrolimus (FK-506), sirolimus (rapamycin), azathioprine, mycophenolate mofetil); angiogenic agents: vascular endothelial growth factor (VEGF), fibroblast growth factor (FGF); angiotensin receptor blockers; nitric oxide donors; anti-sense oligionucleotides and combinations thereof; cell cycle inhibitors, mTOR inhibitors, and growth factor receptor signal transduction kinase inhibitors; retenoids; cyclin/CDK inhibitors; HMG co-enzyme reductase inhibitors (statins); and protease inhibitors.

Although shown and described is what is believed to be the most practical and preferred embodiments, it is apparent that departures from specific designs and methods described and shown will suggest themselves to those skilled in the art and may be used without departing from the spirit and scope of the invention. The present invention is not restricted to the particular constructions described and illustrated, but should be constructed to cohere with all modifications that may fall within the scope of the appended claims.

What is claimed is:

1. A process for coating implantable medical devices comprising:
   (a) applying a primer coating on the implantable medical devices, including the application of a parylene layer and annealing the parylene layer to reduce autoxidation initiators;
   (b) preparing a basecoat solution comprising polymers and a therapeutic agent and applying the basecoat solution to the implantable medical devices coated with parylene, the basecoat solution being prepared with and applied utilizing a process to reduce the presence and exposure of the basecoat solution to oxygen, the implantable medical device with basecoat is dried with recirculating air for at least 30 minutes at a relative humidity of about 30 to about 55 percent;
   (c) preparing a topcoat solution comprising at least one polymer and applying the topcoat solution to the implantable medical devices coated with the basecoat solution, the topcoat solution being prepared with and applied utilizing a process to reduce the presence and exposure of the topcoat solution to oxygen;
   (d) applying toluene that has the potential to redissolve the coating components and alter the surface finish and the dissolution properties of the therapeutic agent, and drying the implantable medical device with topcoat and toluene with recirculating air for at least 30 minutes at a relative humidity of about 30 to about 55 percent;
   (e) reducing the solvent content thereby raising the glass transition temperature of the therapeutic agent and creating a coating morphology to protect the therapeutic agent from autoxidation; and
   (f) finally processing the implantable medical devices, including inspecting, packaging and sterilizing the coated medical devices, the final processing including protecting the therapeutic agent from autoxidation, reducing the presence of and exposure of all materials to radicals and reducing the presence of and exposure of all materials to oxygen.

2. The process according to claim 1, further comprising providing higher glass transition temperatures by minimizing exposure to solvents after drying.

3. The process according to claim 1, further comprising storing the medical devices in a solvent-free environment.

4. The process according to claim 1, further comprising increasing removal of residual solvents by allowing a predetermined period of time to elapse for removal thereof post-coating.

5. The process according to claim 1, further comprising applying vacuum and heat to enhance residual solvent removal.

6. The process according to claim 1, further comprising increasing removal of residual solvents by reducing the water content.

7. The process according to claim 1, wherein final processing further comprises vacuum packaging under inert gas.

8. The process according to claim 1, further comprising minimizing the presence or exposure to free radicals and autoxidation initiators by using materials with minimal free radicals.

9. The process according to claim 8, further comprising using tools comprised of inert materials.

10. The process according to claim 8, further comprising minimizing the presence or exposure to oxygen by using raw materials without free radicals or radical initiators and solvents with low hydroperoxide content.

11. The process according to claim 10, further comprising minimizing decanting of coating solutions and solvents.

12. The process according to claim 11, further comprising blanketing with inert gas to reduce dissolved oxygen.

13. The process according to claim 12, further comprising decreasing levels of oxygen by processing in a nitrogen rich environment.

14. The process according to claim 13, further comprising packaging under inert gas.

15. The process of claim 1, wherein the basecoat is applied to the medical device at once.

16. The process of claim 1, wherein the basecoat is applied to the medical device incrementally.

17. The process according to claim 1, wherein the topcoat is applied to the medical device at once.

18. The process according to claim 1, wherein the topcoat is applied to the medical device incrementally.

* * * * *